United States Patent
Cense et al.

(10) Patent No.: US 6,706,035 B2
(45) Date of Patent: Mar. 16, 2004

(54) SKIN TREATING DEVICE COMPRISING A PROCESSOR FOR DETERMINATION OF THE RADIATION PULSE DOSE

(75) Inventors: Abraham Josephus Cense, Cambridge, MA (US); Xiang Sheng Cheng, Eindhoven (NL)

(73) Assignee: Koninklijke Phillips Electronics N.V., Eindhoven (NL)

( * ) Notice: Subject to any disclaimer, the term of this patent is extended or adjusted under 35 U.S.C. 154(b) by 0 days.

(21) Appl. No.: 10/201,669

(22) Filed: Jul. 23, 2002

(65) Prior Publication Data

US 2003/0023235 A1 Jan. 30, 2003

(30) Foreign Application Priority Data

Jul. 27, 2001 (EP) ............................................. 01202872

(51) Int. Cl.$^7$ ............................................. A61B 18/18
(52) U.S. Cl. ............................. 606/9; 606/12; 607/89
(58) Field of Search ........................ 606/9–12; 607/88, 607/89

(56) References Cited

U.S. PATENT DOCUMENTS 6,074,382 A * 6/2000 Asah et al. ..................... 606/9
6,436,127 B1 * 8/2002 Anderson et al. ............. 607/89
6,641,578 B2 * 11/2003 Mukai ............................ 606/9

FOREIGN PATENT DOCUMENTS

| EP | 1031324 | * | 8/2000 | ........... A61B/18/20 |
| EP | 1031324 A1 | | 8/2000 | ........... A61B/18/20 |
| WO | WO0062700 | | 10/2000 | |
| WO | WO 00/62700 | * | 10/2000 | ........... A61B/18/20 |

* cited by examiner

Primary Examiner—Michael Peffley (57) ABSTRACT

A device for the treatment of skin by radiation. The device has a housing with a radiation source, a control unit, and a detector for detecting an image of the skin. The control unit has a processor which determines from the image a dimension and color of a target object to be treated, and determines from the dimension and color a pulse dose of the radiation source necessary for treating the target object. The device may be a laser epilator used to destroy a root of a hair based on the thickness of the hair root and the color of the hair. The device can also be configured as a laser shaver, delivering a pulse dose necessary to cut a hair based on the thickness and color of the hair.

20 Claims, 3 Drawing Sheets

SKIN TREATING DEVICE COMPRISING A PROCESSOR FOR DETERMINATION OF THE RADIATION PULSE DOSE

The invention relates to a device for treating skin by means of radiation pulses, which device comprises a housing, a radiation source, a control unit for controlling the radiation source, and a detector for detecting an image of at least a part of the skin, said control unit comprising a processor which, in operation, determines from the image detected by the detector a dimension of a target object to be treated on the skin and which determines from said dimension a pulse dose of the radiation source that is necessary to treat said target object.

A device of the type mentioned in the opening paragraph is known from EP-A-1 031 324. The known device is an epilation device. The radiation source used in the known device is a laser source whose wavelength is readily absorbed by melanin, which is a pigment that is present in large concentrations in hairs and hair roots. The device further comprises a laser beam manipulator that is equipped with a number of tiltable mirrors by means of which, in operation, a laser beam generated by the laser source is positioned in a target position on the skin to be treated. The detector used in the known device comprises a heat image sensor. In the known device, prior to the epilation process, the skin is exposed to a diffuse laser beam having a comparatively low dose, after which a heat image of the irradiated skin is detected by means of the detector. By virtue of the large concentrations of melanin in the hair roots, said hair roots and the skin directly surrounding the hair roots are heated more strongly by the diffuse laser beam than other parts of the skin, so that the hair roots show as heat spots on the heat image. The processor subsequently determines the positions and thicknesses of the individual hair roots from the positions and dimensions of the heat spots in the heat image. Subsequently, the processor controls the laser beam manipulator in such a manner that the laser beam is present successively in the positions of the hair roots thus determined, the laser source being activated in each one of said positions by the control unit so as to generate a radiation pulse having a comparatively high pulse dose. The pulse dose necessary to destroy a hair root is determined by the control unit for each individual hair root from the thickness of the relevant individual hair root determined from the heat image. As the processor determines the necessary pulse dose for each individual hair root, in this known epilation device the total amount of radiation energy of the laser source that is necessary to remove all hairs is limited, and pulse doses that are too high leading to unnecessary skin irritations or even skin injuries and to an unnecessarily high energy consumption of the epilation device are precluded as much as possible.

A drawback of the known device resides in that the pulse doses of the laser source that are necessary to destroy individual hair roots are often insufficiently accurately determined by the processor. As a result, in many cases too low a pulse dose is applied so that a hair root is not, or only partly, destroyed and the result of the epilation operation is insufficient, or conversely, the pulse dose applied is too high, as a result of which the hair root is destroyed but also part of the skin tissue around the hair root is adversely affected, thereby causing skin irritations.

It is an object of the invention to provide a device of the type mentioned in the opening paragraph, wherein the pulse dose necessary to treat a target object present in or on the skin can be more accurately determined so that pulse doses of the radiation source that are either too high or too low can be precluded more effectively and a more satisfactory result of the treatment with fewer skin irritations is achieved.

To achieve this object, a device of the type mentioned in the opening paragraph is characterized in accordance with the invention in that the processor also determines from the detected image a color of the target object to be treated, the processor determining the necessary pulse dose from said dimension and said color. It has been found that in many cases the pulse dose that is necessary to treat a target object present on or in the skin depends not only on the dimension (s) of the target object but is predominantly determined by said dimension(s) and by the absorption coefficient of the target object for the radiation generated by the radiation source. The necessary pulse dose is generally lower as said absorption coefficient is higher. It has been found that in many cases, such as in the case of hairs and blood vessels, said absorption coefficient is strongly related to the color of the target object. As, in the device in accordance with the invention, the processor determines from the detected image of the skin not only the dimension of each individual target object but also the color of each individual target object, said processor is capable of additionally determining, for example by means of a previously empirically determined relationship between the color and the absorption coefficient of target objects of the type to be treated, the absorption coefficient of each individual target object by means of the detected image. In this manner, the absorption coefficient of each individual target object is determined in a particularly efficient and practical way. As the processor determines the necessary pulse dose from said dimension and said color that is related to the absorption coefficient, the pulse dose necessary to treat each individual target object is accurately determined, so that pulse doses that are too high or too low are more effectively precluded.

A particular embodiment of a device in accordance with the invention is characterized in that the radiation source comprises a laser source and the device is provided with a laser beam manipulator that can be controlled by the control unit, which laser beam manipulator is used to position a laser beam supplied by the laser source in a target position on the skin, the processor determining from the detected image also a position and/or orientation on the skin of the target object and said processor determining the target position from said position and/or orientation, and the control unit activating the laser source if the laser beam manipulator is in a position that corresponds to the target position. As the target position of the laser beam is determined by the control unit in the manner described above, and the laser source is activated as described above by the control unit if the laser beam manipulator is in a position that corresponds to the target position of the laser beam, determination of the target position and activation of the laser source in the target position occur fully automatically, so that the device is safe for use by inexperienced persons and in particular suitable for the consumer market. To determine the target position from the image of the skin detected by the detector, the control unit comprises for example an algorithm which is suitable for this purpose, and by means of which the position and/or orientation of the target object to be treated on or in the skin can be determined on the basis of the image information, and by means of which the target position can be determined on the basis of said position and/or orientation of the target object. In this manner, by means of the detected image, the dimension and the color of the target object to be treated as well as the target position of the laser beam on the skin is determined, so that the detector is used in a practical and efficient manner.

A further embodiment of a device in accordance with the invention is characterized in that the detector comprises a CCD image sensor or a CMOS image sensor. Said detectors have comparatively small dimensions and are very accurate. The CMOS image sensor has the additional advantage that the electronics necessary to read and interpret the detected image can be integrated in the image sensor, thus leading to a simplification of the structure of the device.

Yet another embodiment of a device in accordance with the invention is characterized in that the processor determines the color of the target object to be treated from a gray value that the target object has in the image of the skin detected by means of the image sensor. In this embodiment use is made of a comparatively simple, low-cost image sensor, and the detected image comprises a comparatively simple gray scale distribution. It has been found that in most cases satisfactory results are achieved by using such a simple image sensor.

A particular embodiment of a device in accordance with the invention is characterized in that the device is a hair removing device, wherein the processor determines from the detected image a thickness and a color of a hair to be removed, and the detector determines from said thickness and color a pulse dose that is necessary to remove said hair. In this embodiment of the device in accordance with the invention, the invention becomes effectual in a particular way because the absorption coefficient of hairs for the radiation of the radiation source depends substantially on the color of the hairs. To remove or cut hairs by means of radiation pulses, use is generally made of a laser source having a wavelength that is absorbed well by melanin, which is a natural pigment present in hairs. Dark hairs generally have a comparatively high concentration of melanin, while fair hairs generally have a lower concentration of melanin. As a result, hairs demonstrate a strong relationship between the color and the absorption coefficient for the applied laser radiation, so that the absorption coefficient can be accurately and reliably determined from the color of the hairs. By virtue thereof, the pulse dose of the laser source that is necessary to remove or cut hairs can be determined in an accurate and reliable manner for each individual hair.

A further embodiment of a device in accordance with the invention is characterized in that the device is a shaver, wherein the processor determines the thickness and the color of a hair to be cut close to a position on the hair where the hair projects from the skin. It has been found that the pulse dose that is necessary to cut a hair near the surface of the skin depends mainly on the thickness of the hair near the surface of the skin and on the absorption coefficient/color of the hair. As the processor determines the thickness and the color of the individual hairs in said position near the surface of the skin, the necessary pulse dose for each individual hair is determined in an accurate and reliable manner. As a result, the shaving performance of the device in this embodiment is satisfactory, and skin irritations are limited as much as possible.

A still further embodiment of a device in accordance with the invention is characterized in that the device is an epilation device, wherein the processor determines a thickness of the hair root from the thickness of the hair by means of a predetermined relationship between hair thickness and hair root thickness, and wherein the processor determines the necessary pulse dose from the color and from the hair root thickness thus determined. It has been found that the pulse dose that is necessary to destroy a hair root depends mainly on the thickness of the hair root and on the absorption coefficient/color of the hair. As hairs generally demonstrate a strong relationship between the thickness of the hair and the thickness of the hair root, in this embodiment the thickness of each individual hair root is determined in a practical and reliable manner by the processor from the thickness of the visible portion of the relevant hair, so that the necessary pulse dose for destroying each individual hair is determined also in an accurate and reliable manner by the processor. As a result, the epilation performance of the device in this embodiment is satisfactory, and skin irritations are limited as much as possible.

These and other aspects of the invention will be apparent from and elucidated with reference to the embodiment(s) described hereinafter.

Figure 1:
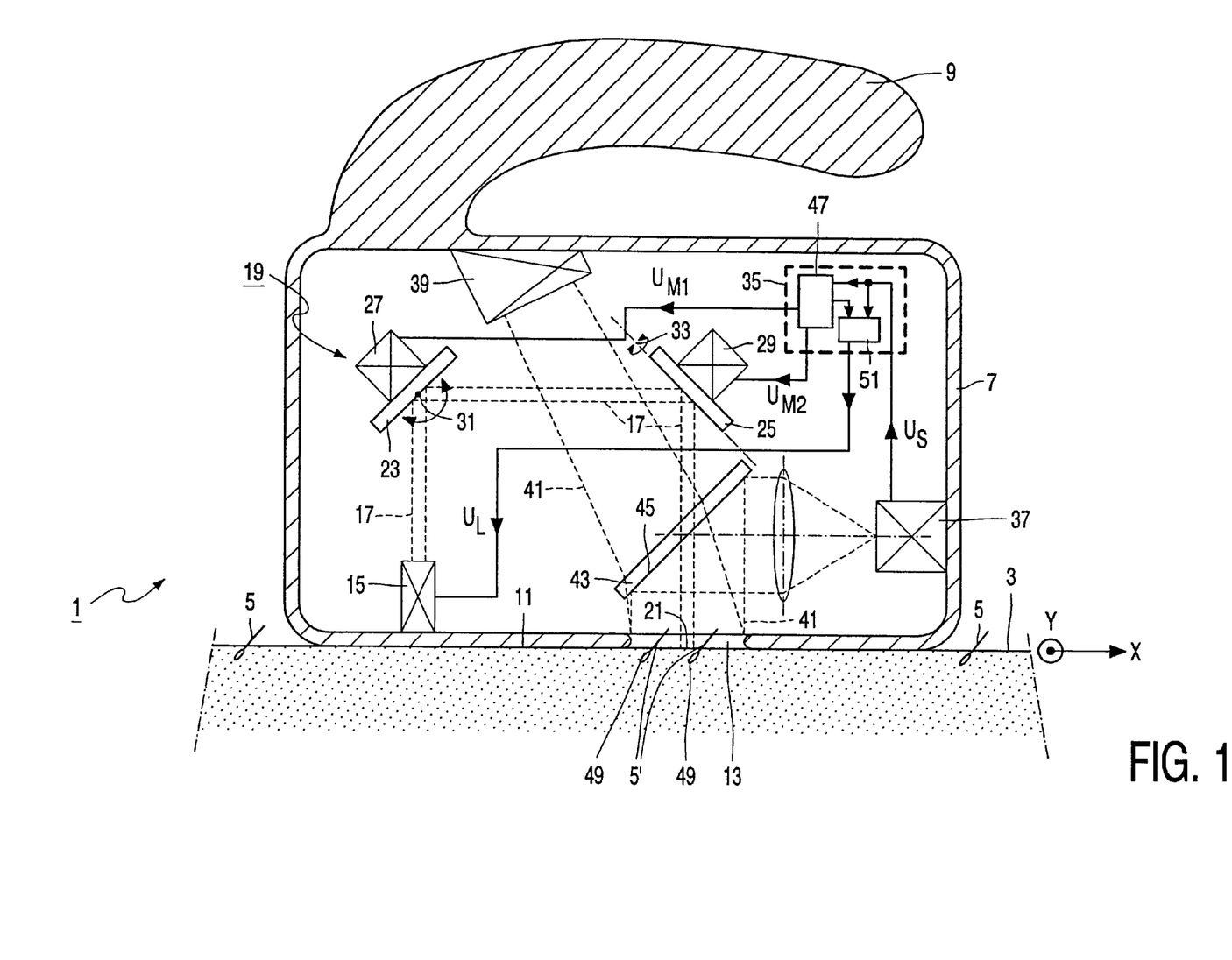
FIG. 1 diagrammatically shows a first embodiment of a device in accordance with the invention for treating skin by means of radiation pulses, FIG. 2 diagrammatically shows a part of an image of the skin, which is detected by a detector of the device in accordance with FIG. 1, FIG. 3 diagrammatically shows a second embodiment of a device in accordance with the invention for treating skin by means of radiation pulses, and FIG. 4 diagrammatically shows a part of an image of the skin, which is detected by a detector of the device in accordance with FIG. 3.

FIG. 1 diagrammatically shows a first embodiment of a device 1 in accordance with the invention for treating skin 3 by means of radiation pulses, said device being a hair removing device, in particular a laser epilation device, by means of which hairs 5 present on the skin 3 are removed for a comparatively long period of time, or permanently, by means of laser pulses. Said device 1 comprises a housing 7 with a handle 9, so that the device 1 is portable and can be placed on or moved over skin 3 to be treated. The housing 7 has a skin contact surface 11 via which the housing 7 is in contact with the skin 3 during operation. The skin contact surface 11 is equipped with an exit opening 13. The housing 7 accommodates a radiation source 15, which, in the embodiment shown, is a laser source such as a diode laser. The radiation source 15 generates, in operation, a laser beam 17 having a frequency that is absorbed well by melanin, which is a natural pigment present in large concentrations in hairs. A suitable wavelength lies in the range between for example 650 nm and 1200 nm. The housing 7 further accommodates an adjustable laser beam manipulator 19 by means of which, in operation, the laser beam 17 can be positioned, via the exit opening 13, in a target position 21 on the skin 3. In the embodiment shown, the laser beam manipulator 19 is equipped with a first adjustable tilting mirror 23 and a second adjustable tilting mirror 25, which are both arranged at an angle of approximately 45° with respect to the skin contact surface 11. By means of, respectively, a first actuator 27 and a second actuator 29, the tilting mirrors 23 and 25 can be tilted about, respectively, a first tilt axis 31, which extends in the plane of the first tilting mirror 23 and is directed substantially parallel to the skin contact surface 11, and a second tilt axis 33, which extends in the plane of the second tilting mirror 25 and crosses the first tilt axis 31 substantially perpendicularly. By tilting the tilting mirrors 23 and 25, the target position 21 of the laser beam 17 can be displaced over the skin 3 in a direction parallel to an X-direction and a Y-direction extending perpendicularly thereto, both directions being parallel to the skin contact surface 11.

The housing 7 further accommodates a control unit 35 by means of which the actuators 27 and 29 and the radiation source 15 can be controlled in the following manner. The control unit 35 receives, in operation, a signal $u_s$ that is supplied by a detector 37, i.e. a CMOS image sensor in the embodiment shown. Prior to the epilation process, the detector 37 detects an image of the part of the skin 3 that is situated in front of the exit opening 13. To this end, said part of the skin 3 is exposed by means of an illumination member 39 that is also accommodated in the housing 7 and that supplies a light beam 41 via a transparent plate 43 that is provided with a reflective surface 45 on a side facing the exit opening 13. The control unit 35 is equipped with a first processor 47 which determines from the signal $u_s$, i.e. from the image of the skin 3 detected by the detector 37, the positions of the hair roots 49 of the hairs 5' present on the relevant part of the skin. Subsequently, the first processor 47 controls the actuators 27 and 29 by means of, respectively, a signal $u_{M1}$ and a signal $u_{M2}$ in such a manner that the laser beam 17 is successively positioned in a series of target positions 21 that correspond to the positions of the hair roots 49 determined by the first processor 47. In each one of the target positions 21, the radiation source 15 is activated by the first processor 47 by means of a signal $U_L$ so as to generate a laser pulse with a pulse dose that is determined in a manner that will be described hereinbelow by a second processor 51 of the control unit 35. For each hair root 49 the pulse dose is so high that the relevant hair root dies. As the target positions 21 are automatically determined as described above by the control unit 35, and activation of the radiation source 15 by the control unit 35 takes place only in said target positions, safe operation of the device 1 is ensured and said device is particularly suitable for use by non-professional users, i.e. it is suitable for the consumer market. For a detailed explanation of the operation of the device 1, which has only been briefly described hereinabove, and in particular for an explanation of the way in which the control unit 35 determines the target positions 21 from the image detected by the detector 37 and controls the laser beam manipulator 19 and the radiation source 15, reference is made to WO-A-00/62700, which explanation may be considered to be incorporated in this description.

Figure 2:
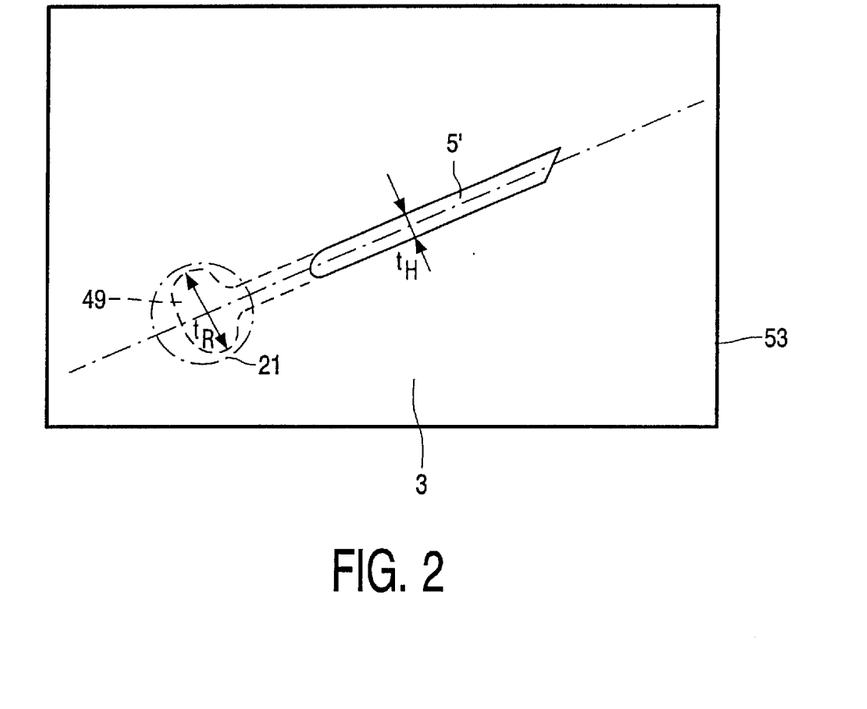

The pulse dose of the laser beam 17 is determined individually for each hair root 49 by the second processor 51 of the control unit 35. It has been found that the pulse dose that is necessary to cause a hair root to be destroyed and die depends predominantly on the thickness of said hair root and on the absorption coefficient of the hair for the laser light supplied by the laser source 15. The necessary pulse dose is higher as said thickness is greater, and the necessary pulse dose is lower as said absorption coefficient is higher. As said absorption coefficient is predominantly determined by the concentration of melanin in a hair, and the color of a hair is predominantly determined by said concentration, hairs demonstrate a strong relationship between the color and said absorption coefficient. Dark hairs have a comparatively high concentration of melanin, so that the necessary pulse dose for dark hairs is comparatively low. Fair hairs have a comparatively low concentration of melanin, so that the necessary pulse dose is comparatively high. As will be explained hereinbelow, this relationship is used by the second processor 51 to determine the pulse dose. As shown in FIG. 1, the second processor 51 receives the signal $u_s$ that corresponds to the image of the skin 3 detected by the detector 37. In the example shown, the signal $u_s$ comprises a series of 8-bit gray values of the pixels of the detector 37. FIG. 2 diagrammatically shows a sub-region 53 of the image detected by the detector 37, which sub-region comprises a hair 5'. The second processor 51 determines a gray-value distribution of the detected image, from which the second processor 51 determines the thickness $t_H$ for each individual hair 5' present in the image and, by means of a predetermined relationship between the color of the hair and the gray value of hairs in such an image, the color. The thickness of each individual hair 5', which is determined as described above, is used by the second processor 51 to determine the thickness $t_R$ of the hair root 49 of the relevant hair 5' by means of a previously empirically established relationship between the hair thickness and the hair root thickness. As hairs demonstrate a strong relationship between the hair thickness and the hair root thickness, the thickness of the hair root 49 is reliably determined in this manner by the second processor 51 from the thickness of the visible part of the hair 5'. The thus determined thickness of the hair root 49 and the color are used by the second processor 51 to subsequently determine, for each individual hair 5' present in the image, the necessary pulse dose from the radiation source 15 by means of a previously empirically established relationship between the pulse dose, the hair root thickness and the color of the hair. As the necessary pulse dose depends strongly on the hair root thickness as well as the color of the hair, the pulse doses necessary to destroy the hair roots 49 are accurately and reliably determined in this way. The control unit 35 activates the laser source 15 in each target position 21 determined by means of the first processor 47, the pulse dose being determined, as described above, by the second processor 51 for the hair root 49 present in the relevant target position 21. As the thickness of hair roots and the color of hairs differ from person to person, the total amount of radiation energy needed by the device 1 to treat all hair roots 49 is smaller that the total amount of radiation energy needed by a conventional laser epilation device whose pulse dose has a constant value that is so high that statistically the commonest hair root types are destroyed. As the control unit 35 determines the necessary pulse dose from the radiation source 15 for each individual hair root 49, it is precluded, on the one hand, that the relevant hair root 49 is exposed to too high a pulse dose, as a result of which not only the hair root 49 would be affected but also the surrounding skin tissue, which could lead to skin irritations, and, on the other hand, it is precluded that the relevant hair root 49 is exposed to too low a pulse dose, as a result of which the hair root would not be destroyed completely and the epilation result could not be optimal. As a result, the epilation device 1 in accordance with the invention yields comparatively good epilation results, while causing no, or comparatively few, skin irritations.

Since, as described above, the control unit 35 derives not only the positions of the hair roots 49 that are necessary to determine the target positions 21 of the laser beam manipulator 19 from the image of the skin 3 detected by the detector 37, but also the thickness and color of each hair 5' that are necessary to determine the necessary pulse doses, the detector 37 is efficiently used. In the embodiment described above, the detector 37 comprises a comparatively simple and inexpensive CMOS image sensor, and the detected image has a comparatively simple gray-value distribution of the skin 3. It has been found that the results achieved by such an image sensor are mostly satisfactory. The reliability with which the absorption coefficient-related color of the hairs 5' can be determined from the gray-value distribution increases considerably if the light from the illumination member 39, to which the skin is exposed, has a wavelength that corresponds to the wavelength of the radiation source 15. A CMOS image sensor has the additional advantage that the electronics necessary to read and interpret the detected image can be integrated in the image sensor. By virtue thereof, the control unit 35 can be integrated partly, or even bodily, with the detector 37, resulting in a substantial simplification of the structure of the device 1. It is noted that the invention also comprises embodiments wherein the device is equipped with a different type of detector for detecting an image of the skin. For example, the detector may comprise a CCD image sensor instead of a CMOS image sensor. The invention, for example, also comprises embodiments wherein the detector comprises a heat image sensor, as is the case in the epilation device known from EP-A-1 031 324. In this alternative embodiment, the control unit of the device is adapted in a manner that is known per se so as to enable reading and interpreting the image of the skin detected by means of the alternative detector used.

Figure 3:
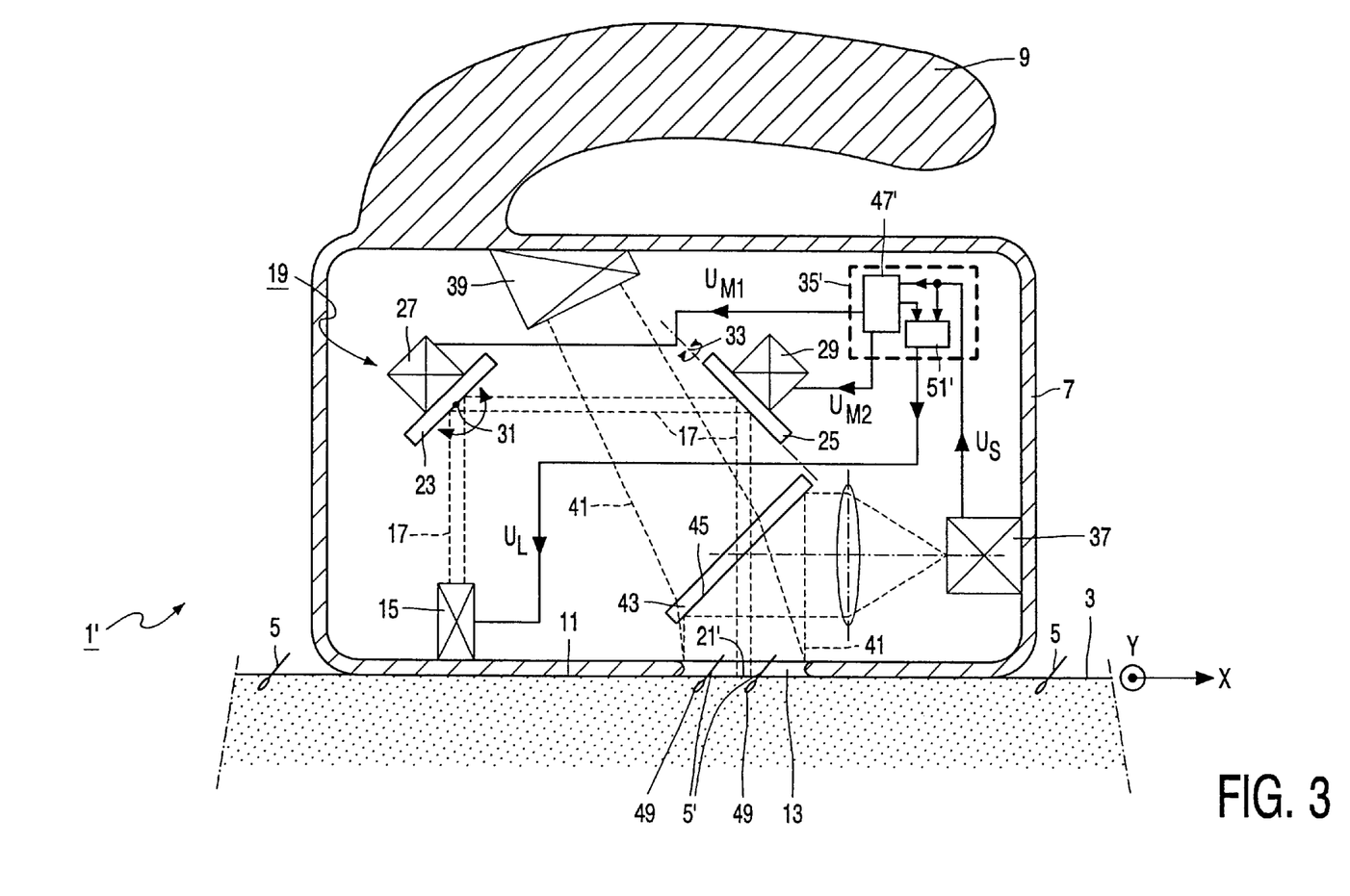

FIG. 3 diagrammatically shows the second embodiment of a device 1' in accordance with the invention for treating skin 3 by means of radiation pulses, said device also being a hair removing device, in particular a laser shaving device, by means of which hairs 5 present on the skin 3 are cut close to the surface of the skin. In FIG. 3, parts of the device 1' corresponding to parts of the device 1 described hereinabove are indicated by means of corresponding reference numerals. Hereinbelow only the most important differences between the device 1' and the device 1 are discussed.

Figure 4:
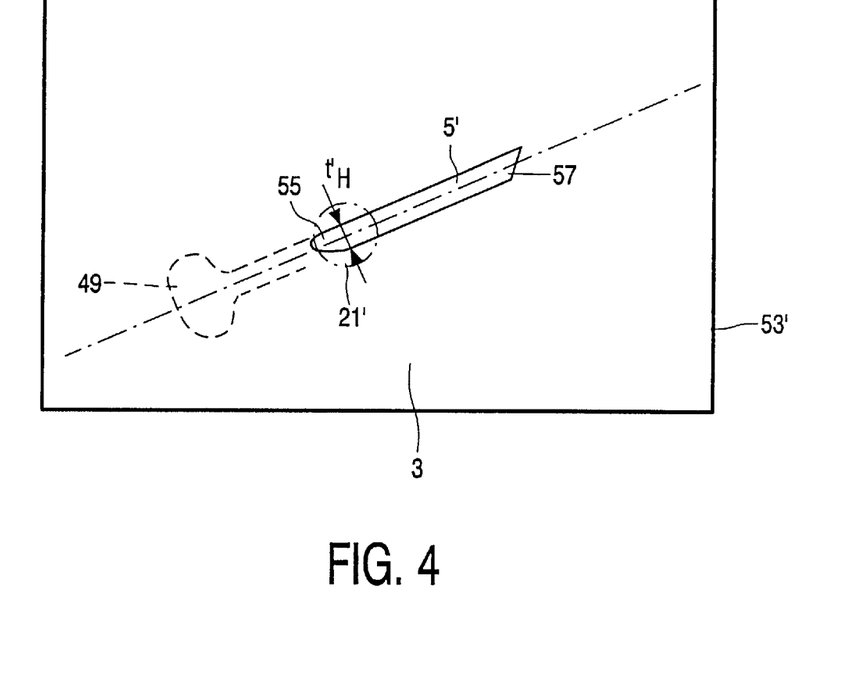

The device 1' differs mainly from the device 1 in that the first processor 47' of the control unit 35' employed in the device 1' determines the target positions 21' of the laser beam 17 in a different manner and in that the second processor 51' of the control unit 35' determines the necessary pulse doses of the radiation source 15 in a different manner. FIG. 4 diagrammatically shows a sub-region 53' of the image detected by the detector 37, wherein a hair 5' is present. The first processor 47' determines, from the gray-value distribution of the detected image, a position 55 on the hair 5' where said hair 5' projects from the skin 3. When the first processor 47' determines the position 55 it makes a distinction between the position 55 and the end 57 of the hair 5' by means of previously determined gray-value characteristics and form characteristics of hair-emergence positions and hair ends that are stored in the memory of the first processor 47'. The first processor 47' thus determines the relevant position 55 for each hair present in the image. Subsequently, the first processor 47' controls the actuators 27 and 29 by means of, respectively, the signals $u_{M1}$ and $u_{m2}$ in such a manner that the laser beam 17 is successively positioned in a series of target positions 21' that correspond to positions on the hairs 5' close to the positions 55 thus determined by the second processor 47'. In each of the target positions 21' the radiation source 15 is activated by the first processor 47' by means of the signal $u_L$ to generate a laser pulse having a pulse dose that is determined by the second processor 51' in a manner that will be described in more detail hereinbelow. For each hair 5' the pulse dose is so high that the relevant hair 5' is cut close to the position 55, i.e. near the surface of the skin. It is noted that the device 1' can be provided with an adjusting member enabling the user to set the location of the target positions 21' with respect to the surface of the skin 3. Said adjusting member enables the user, for example, to set a location of the target positions 21' at skin surface level or even below the surface of the skin 3, so that a very smooth shaving result is obtained, or a location just above the surface of the skin 3 or even at some distance above the surface of the skin 3, so that during shaving a predetermined length of the hairs 5' above the surface of the skin 3 is maintained. In this manner, the desired smoothness can be obtained by setting said adjusting member. It is further noted that in the device 1', the pulse dose that is necessary to cut the hairs 5, 5' by means of the laser beam 17 is much lower than the pulse dose that is necessary to destroy the hair roots 49 in the device 1 described hereinabove. Thus, the necessary power from the radiation source 15 of the device 1' is much smaller that the necessary power from the radiation source 15 of the device 1.

The pulse dose of the laser beam 17 that is necessary to cut an individual hair 5' close to the surface of the skin 3 depends substantially on the thickness of the relevant hair 5' and on the absorption coefficient of the hair 5' for the laser light supplied by the radiation source 15, said absorption coefficient being strongly related to the color of the hair 5'. The second processor 51' determines, from the gray-value distribution of the image of the skin 3 detected by means of the detector 37, and by means of the predetermined gray-value characteristics and form characteristics of hair-emergence positions and hair ends that are stored in the memory of the first processor 47', for each individual hair 5' present in the image the thickness $t'_H$ and the color in the position 55 on the relevant hair 5' where said hair 5' emerges from the skin 3. The thickness $t'_H$ and the color thus determined are used by the second processor 51' to subsequently determine, for each individual hair 5' present in the image, the necessary pulse dose from the radiation source 15 by means of a previously empirically established relationship between the pulse dose, the hair thickness and the hair color. As the necessary pulse dose depends substantially on the hair thickness as well as the hair color, the pulse doses that are necessary to cut the hairs 5' are particularly accurately and reliably determined in the manner described above. The control unit 35' activates the laser source 15 in each target position 21' determined by means of the first processor 47', the pulse dose being determined, as described above, by the second processor 51' for the hair 5' present in the relevant target position 21'.

The above-discussed devices 1 and 1' are hair removing devices by means of which hair roots are destroyed or hairs are cut using a laser beam that is positioned in a target position on the hairs by means of a laser beam manipulator. It is noted that the invention also comprises other types of devices for treating other types of target objects present in or on the skin by means of radiation pulses. Examples of such devices are devices for the medical or cosmetic treatment by means of radiation pulses of birthmarks, such as naevus vinosus and naevus pigmentosus, present on the skin, psoriasis, or aberrations of blood vessels present in the skin, such as varicose veins. In such alternative devices, the image of the skin detected by means of the detector is used to establish a pulse dose-determining dimension and the color/absorption coefficient of the target object to be treated, and the necessary pulse dose is subsequently determined from the dimension and color thus determined. For example, in a device for treating aberrations of blood vessels present in the skin, the thickness of the relevant blood vessels is the dimension that determines the pulse dose.

It is further noted that the invention also comprises devices for treating skin by means of radiation pulses which are equipped with a type of radiation source that differs from the laser source applied in the above-described devices 1 and 1'. Examples of such devices are flashlights, in which case the necessary pulse dose must also be determined from a characteristic dimension and color of the target object to be treated. If such a flashlight is used, the part of the skin present in front of the exit opening of the housing is completely irradiated by the flashlight, so that such a device does not require a radiation beam manipulator.

The pulse dose that is determined by the second processor 47, 47' of the devices 1, 1' is a minimum pulse dose necessary to destroy the hair roots 49 or cut the hairs 5, 5'. It is noted that a device in accordance with the invention can also be provided with a further processor that determines a maximum permissible pulse dose of the radiation source for the skin, for example, on the basis of a value or state of a biophysical property of the skin measured by means of a further detector. A biophysical property of the skin enabling the maximum permissible pulse dose to be determined is, for example, the absorption coefficient, the scattering coefficient or the reflection coefficient of the skin for the radiation of the radiation source. In such an embodiment of a device in accordance with the invention, not only a minimum pulse dose necessary to treat the target object present in or on the skin is determined in this manner but also a maximum permissible pulse dose for the skin. Such a device can be equipped, for example, with a protection that makes sure that the radiation source is not activated in situations where the minimum pulse dose thus determined exceeds the maximum permissible pulse dose.

What is claimed is:

1. A device for treating skin by radiation comprising a housing, a radiation source, a control unit controlling the radiation source, and a detector detecting an image of at least a part of the skin, said control unit comprising a processor, the processor being configured to determine, in operation of the radiation source during treatment, from the image detected by the detector, a dimension of a target object to be treated on the skin and, from said dimension, a pulse dose of the radiation source that is necessary to treat said target object, wherein the processor is also configured to determine from the detected image a color of the target object to be treated, and to determine from said dimension and said color, the necessary pulse dose.

2. A device as claimed in claim 1, wherein the radiation source comprises a laser source and the device is provided with a laser beam manipulator that can be controlled by the control unit, which laser beam manipulator is used to position a laser beam supplied by the laser source in a target position on the skin, the processor determining from the detected image also a position and/or orientation on the skin of the target object and said processor determining the target position from said position and/or orientation, and the control unit activating the laser source if the laser beam manipulator is in a position that corresponds to the target position.

3. A device as claimed in claim 1, wherein the detector comprises a CCD image sensor.

4. A device as claimed in claim 3, wherein the color of the target object to be treated is a gray value.

5. A device as claimed in claim 1, wherein the target object is a hair, the dimension is a thickness of the hair, the color is a color of the hair, and the necessary pulse dose is a pulse dose that is necessary to remove said hair.

6. A device as claimed in claim 5, wherein the processor is further configured to determine a position on the hair close to where the hair projects from the skin and the necessary pulse dose is a dose that is necessary to remove said hair by cutting said hair at the position.

7. A device as claimed in claim 1, wherein the target object is a hair, the dimension is a thickness of the hair, and the color is a color of the hair, the processor being configured to store a predetermined relationship between hair thickness and hair root thickness and to determine, from the thickness of the hair, by reference to the predetermined relationship, a value corresponding to a thickness of a root of the hair, and wherein the necessary pulse dose is a pulse dose that is necessary to remove said hair, the processor being further configured to determine the necessary pulse dose from the color and from the value corresponding to the thickness of the root of the hair.

8. A device as claimed in claim 1, wherein the detector comprises a CMOS image sensor.

9. A device for treating skin by radiation pulses comprising:
 a housing having a skin contact surface in contact with the skin during treatment, the skin contact surface having an exit opening,
 a radiation source in the housing,
 a control unit capable of controlling the radiation source, and
 a detector capable of detecting an image of at least a part of the skin, the part being visible to the radiation source through the exit opening,
 the control unit comprising a processor and a program storage device tangibly embodying a program of instructions executable by the processor, the program of instructions being programmed to, during passage of the exit opening over the skin, determine from the image detected by the detector a dimension of a target object to be treated on the skin and to determine from said dimension a pulse dose of the radiation source necessary to treat said target object,
 the processor and program of instructions being further configured to determine from the detected image a detected color corresponding to a color of the target object to be treated, and to determine, from said dimension and said detected color, the necessary pulse dose.

10. A device as claimed in claim 9, wherein the radiation source comprises a laser source and the device is provided with a laser beam manipulator that can be controlled by the control unit, the laser beam manipulator being capable of positioning a laser beam from the laser source on a target position on the skin, the processor being configured to determine from the detected image a position, orientation or position and orientation of the target object and to determine the target position from the position, orientation or position and orientation, and the control unit being capable of activating the laser source if the laser beam manipulator is in a position that corresponds to the target position.

11. A device as claimed in claim 9, wherein the color of the target object to be treated corresponds to a gray value detected by the detector.

12. A device as claimed in claim 9, wherein the target object is a hair, the dimension is a thickness of the hair, the color is a color of the hair, and the necessary pulse dose is a pulse dose that is necessary to remove said hair.

13. A device as claimed in claim 12, wherein the processor is further configured to determine a position on the hair close to where the hair projects from the skin and the necessary pulse dose is a dose that is necessary to remove said hair by cutting said hair at the position.

14. A device as claimed in claim 9, wherein the target object is a hair, the dimension is a thickness of the hair, and the color is a color of the hair, the processor being configured to store a predetermined relationship between hair thickness and hair root thickness and to determine, from the thickness of the hair, by reference to the predetermined relationship, a value corresponding to a thickness of a root of the hair, and wherein the necessary pulse dose is a pulse dose that is necessary to remove said hair, the processor being further configured to determine the necessary pulse dose from the color and from the value corresponding to the thickness of the root of the hair.

15. A device as claimed in claim 9, wherein the detector comprises a CMOS image sensor.

16. A device for treating skin by radiation pulses comprising:

a radiation source, a housing containing the radiation source, a detector capable of detecting an image of the skin, the detector comprising an image sensor, the image sensor comprising a sensor processor, a control unit capable of controlling the radiation source, the control unit comprising a second processor and a program storage device tangibly embodying a program of instructions executable by the sensor processor and the second processor, the program of instructions being programmed to determine from the image detected by the detector a dimension of a target object to be treated on the skin and to determine from said dimension a pulse dose of the radiation source necessary to treat said target object, the sensor processor, second processor and program of instructions being further configured to determine, in operation of the radiation source during treatment, from the detected image, a color of the target object to be treated, and to determine, from the dimension and the color, the necessary pulse dose.

17. A device as claimed in claim 16, wherein the detector comprises a CMOS image sensor.

18. A method for treating skin by radiation comprising:

positioning a portion of the skin at a location visible from an exit opening of a housing containing a radiation source;

detecting an image of at least a part of the portion of the skin;

locating, on the part of the portion of the skin, a target object to be treated;

determining, from the image, a dimension of the target object;

determining, from the image, a color of the target object;

determining from the dimension and the color, a pulse dose of the radiation source necessary to treat the target object; and, while the exit opening is positioned at the location visible to the portion of the skin, positioning the radiation source within the housing to irradiate the target object with the pulse dose.

19. The method of claim 18, wherein the target object is a hair and the pulse does is a dose necessary to treat the hair by cutting.

20. The method of claim 18, wherein the target object is a hair root and the pulse does is a dose necessary to treat the skin by removing the hair root.

* * * * *

UNITED STATES PATENT AND TRADEMARK OFFICE
CERTIFICATE OF CORRECTION

PATENT NO.     : 6,706,035 B2
DATED          : March 16, 2004
INVENTOR(S)    : Cense et al.

It is certified that error appears in the above-identified patent and that said Letters Patent is hereby corrected as shown below:

<u>Title page,</u>
Item [73], Assignee, after "Koninklijke" change "Phillips" to -- Philips --.

Signed and Sealed this

First Day of June, 2004

JON W. DUDAS
*Acting Director of the United States Patent and Trademark Office*